United States Patent [19]

Hill et al.

[11] Patent Number: 5,651,959

[45] Date of Patent: Jul. 29, 1997

[54] ULTRAMULSION BASED ORAL CARE COMPOSITIONS

[75] Inventors: Ira D. Hill, Locust; Peter P. Walters, Neshanic, both of N.J.; Dale G. Brown, Wharton, Tex.

[73] Assignee: WhiteHill Oral Technologies, Inc., Chadds Ford, Pa.

[21] Appl. No.: 462,203

[22] Filed: Jun. 5, 1995

[51] Int. Cl.$^6$ .................................................. A61K 7/16
[52] U.S. Cl. .......................... 424/49; 132/321; 132/323; 424/401; 433/216; 433/217.1
[58] Field of Search ............... 424/401, 49; 132/321, 132/323; 433/216, 217.1

[56] References Cited

U.S. PATENT DOCUMENTS

| | | | |
|---|---|---|---|
| 2,667,443 | 1/1954 | Ashton | 167/93 |
| 2,748,781 | 6/1956 | Collat | 132/93 |
| 2,806,814 | 9/1957 | Richter | 167/93 |
| 2,941,926 | 6/1960 | Salzmann | 167/93 |
| 3,137,632 | 6/1964 | Schiralki | 167/93 |
| 3,219,527 | 11/1965 | Gurney | 167/60 |
| 3,254,714 | 6/1966 | Gogarty | 166/9 |
| 3,307,628 | 3/1967 | Sena | 166/9 |
| 3,339,546 | 9/1967 | Chen | 128/156 |
| 3,417,179 | 12/1968 | Roth | 434/28 |
| 3,429,963 | 2/1969 | Shedlovsky . | |
| 3,429,964 | 2/1969 | Rieger | 424/73 |
| 3,433,780 | 3/1969 | Cekada, Jr. et al. | 260/29.2 |
| 3,497,006 | 2/1970 | Jones et al. | 166/273 |
| 3,506,070 | 4/1970 | Jones | 166/273 |
| 3,507,955 | 4/1970 | Osipow | 424/54 |
| 3,624,120 | 11/1971 | Yetter et al. . | |
| 3,678,154 | 7/1972 | Widder et al. | 424/52 |
| 3,698,392 | 10/1972 | Vogt et al. | 128/268 |
| 3,737,533 | 6/1973 | Moon et al. | 424/226 |
| 3,911,099 | 10/1975 | DeFoney et al. | 424/28 |
| 3,911,766 | 10/1975 | Fridolph et al. | 76/101 R |
| 3,927,201 | 12/1975 | Baines et al. | 424/54 |
| 3,927,202 | 12/1975 | Harvey et al. | 424/57 |
| 3,942,539 | 3/1976 | Corliss et al. | 132/79 E |
| 3,956,480 | 5/1976 | Dichte et al. | 424/54 |

(List continued on next page.)

OTHER PUBLICATIONS

L. Menaker, The Biologic Basis of Dental Caries, Chapters 5, 11, 12, 14 16 and 18, Harper & Row (1980).
A. Gaffar et al., Journal of Pharm. Sci., vol. 71, No. 11 1228–1230(1985).
Bass, Dent. Items of Interest, 70: 921–34 (1994).
Kornman, Journal of Periodontal Rsch. Supp, 5–22 (1986).
Volpe, Journal of Dental Rsch, 48: 832–841 (1969).
Gjermo et al., Journal of Periodontal Rsch, 5:102–109 (1970).
Fornell et al., Scand. Journal of Dental Rsch, 83: 18–25 (1975).

(List continued on next page.)

*Primary Examiner*—Terressa Mosley
*Attorney, Agent, or Firm*—Ernest V. Linek

[57] ABSTRACT

The present invention relates to various oral care products containing, stable, dispersions of certain high viscosity silicones in certain surfactants; wherein:

a. the dispersed silicones, which are insoluble in said surfactant, are oriented by the surfactant such that when dispersed in water they are particularly adept at forming oriented, coatings on surfaces of the mouth with enhanced substantivity, and b. the particle size of the dispersed silicone is from between about 0.1 and about 10 microns, with a particle size distribution such that from between about 80 and 95% of the dispersed silicone is within this particle size range. These stable dispersions are described as ULTRAMULSIONS, which, together with their physical properties, when contained in oral care products, provide these oral care products with enhanced substantivity to mouth surfaces, where the non continuous silicone phase functions as a reservoir for various active ingredients contained therein.

30 Claims, 4 Drawing Sheets

U.S. PATENT DOCUMENTS

| | | | |
|---|---|---|---|
| 3,964,164 | 6/1976 | Hesselgreen . | |
| 3,975,294 | 8/1976 | Dumoulin | 252/354 |
| 4,020,558 | 5/1977 | Cournut et al. | 32/40 R |
| 4,022,880 | 5/1977 | Vinson et al. | 424/54 |
| 4,110,429 | 8/1978 | Gaffer | 424/54 |
| 4,146,499 | 3/1979 | Rosano . | |
| 4,152,416 | 5/1979 | Spitzer et al. | 424/46 |
| 4,175,326 | 11/1979 | Goodson | 433/80 |
| 4,205,061 | 5/1980 | Vidra | 424/55 |
| 4,224,308 | 9/1980 | Gaffar et al. | 424/49 |
| 4,244,931 | 1/1981 | Jarvis et al. | 423/266 |
| 4,247,526 | 1/1981 | Jarvis et al. | 423/266 |
| 4,251,507 | 2/1981 | Olson | 424/49 |
| 4,304,766 | 12/1981 | Chang | 424/52 |
| 4,329,333 | 5/1982 | Barr | 424/19 |
| 4,343,785 | 8/1982 | Schmolka | 424/60 |
| 4,353,890 | 10/1982 | Scott | 424/49 |
| 4,465,661 | 8/1984 | Schmolka | 424/49 |
| 4,465,663 | 8/1984 | Schmolka | 424/62 |
| 4,476,107 | 10/1984 | Schmolka | 424/49 |
| 4,511,563 | 4/1985 | Schmolka | 514/162 |
| 4,525,342 | 6/1985 | Weiss et al. . | |
| 4,537,778 | 8/1985 | Clipper et al. | 424/53 |
| 4,568,535 | 2/1986 | Loesche | 424/19 |
| 4,612,191 | 9/1986 | Yeh et al. | 424/52 |
| 4,620,878 | 11/1986 | Gee | 106/287 |
| 4,657,758 | 4/1987 | Goldemberg et al. | 424/49 |
| 4,661,341 | 4/1987 | Benedict et al. | 424/48 |
| 4,666,708 | 5/1987 | Goldemberg et al. | 424/49 |
| 4,764,377 | 8/1988 | Goodson | 424/435 |
| 4,774,077 | 9/1988 | Ferlando, Jr. | 424/82 |
| 4,892,736 | 1/1990 | Goodson | 424/435 |
| 4,894,220 | 1/1990 | Nabi et al. . | |
| 4,902,497 | 2/1990 | Crisanti et al. | 424/52 |
| 4,911,927 | 3/1990 | Hill et al. | 424/442 |
| 4,933,182 | 6/1990 | Higashi et al. | 424/435 |
| 4,942,034 | 7/1990 | Hill et al. | 424/401 |
| 4,950,479 | 8/1990 | Hill et al. | 424/49 |
| 4,981,693 | 1/1991 | Higashi et al. | 424/438 |
| 5,009,881 | 4/1991 | Hill et al. | 424/49 |
| 5,032,387 | 7/1991 | Hill et al. | 424/49 |
| 5,057,306 | 10/1991 | Hill et al. | 424/49 |
| 5,057,307 | 10/1991 | Hill et al. | 424/49 |
| 5,057,308 | 10/1991 | Hill et al. | 424/52 |
| 5,057,309 | 10/1991 | Hill et al. | 424/52 |
| 5,057,310 | 10/1991 | Hill et al. | 424/52 |
| 5,078,988 | 1/1992 | Lin | 424/49 |
| 5,098,711 | 3/1992 | Hill et al. | 424/401 |
| 5,165,913 | 11/1992 | Hill et al. | 424/49 |
| 5,284,648 | 2/1994 | White et al. | 424/49 |

OTHER PUBLICATIONS

Lusk et al., Journal of the Amer. Society of Preventive Dentistry, 4: 31–37 (1974).

W. Loesche, Chemotherapy of Dental Plaque Infections, Oral Sci. Rev., 9: 65–107 (1976).

Segreto et al., Journal of Dent. Rsch., vol. 40, No. 1, 90–96 (1961).

Mark, Journal of Chemical Physics, vol. 49, No. 3, 1398–1402 (1968).

Liao et al., Journal of Chemical Physics, vol. 59, No. 7, 3825–3830 (1973).

Sutton et al., Journal of Chem. Physics, vol. 54, No. 12, 5011–5014 (1971).

L. Prince, Biological Horizons in Surface Science, p. 361, Academic Press Inc. (1973).

Sumner, T., Theory of Emulsions and Their Technical Treatment, 4th Ed. p. 1, The Blakiston Co., Philadelphia (1943).

W. Noll, Chemistry and Technology of Silicones, pp. 428–431, New York Academic Press (1968).

Mark, Macromolecules, vol. 11, No. 4, 627–633 (1978).

Rowe, The Journal of Industrial Hygiene and Toxicology, vol. 30, No. 6, pp. 332–352 (1948).

N. Vassilakos, Scand. J. Dent. Res., 101:137–7 (1993).

Lindhe, Journal of Clinical Periodontology, 9: 115–128 (1982).

Addy et al., Journal of Clinical Periodontology, 11:467–474 (1984).

Goodson et al., J. Periodontal., vol. 54, No. 10, 575–579 (1983).

Soskoline et al., Journal of Periodontal Rsch, 18: 330–336.

Genco, J. Periontol., vol. 52, No. 9, 545–558 (1981).

Kornman, Journal of Periodontal Rsch., Supp. 5–22 (1986).

Wolfe, Journal of Clinical Periodontology, 3:148–156 (1976).

Bergenholtz et al., J. Clin. Periodontal., 1: 160–165 (1974).

Peterson et al., Northwest Dentistry, 276–278, (1963).

Golomb et al., Journal of Dental Res., 63: 1149–1153 (1984).

Kennedy, Jr. et al., J. Taxicol. & Environmental Health, 1: 909–920 (1976).

J. Slots, Host–Parasite Interactions in Periodontal Disease, 27–45 (1982).

Loesche, Host–Parasite Interactions in Periodontal Disease, 62–75 (1982).

Goodson, J. Medical Applications of Controlled Release, vol. II, Chapter 7, CRC Press, Boca Raton 115–138 (1984).

Rolla et al., Scand. J. Dent., Res., 101: 192–5 (1993).

Mankodi et al., J. of Dental Res., 246 (1988).

Rolla et al., Scand. J. Dent. Res., 101: 130–2 (1993).

McCutheon's Detergents and Emulsifiers, 1979 Annual, published by Allured Publishing Corporation incorporated herein by reference.

Pierre Fauchard in 1746 "The Surgeon Dentist, a Treatise on Teeth".

ULTRAMULSION BASED ORAL CARE COMPOSITIONS

BACKGROUND OF THE INVENTION

The present invention relates to unique oral care compositions containing a dispersion of certain silicones in certain surfactants. When added to water these dispersions are stable and are distinct from solutions, emulsions and microemulsions. These dispersions are referred to hereinafter as ULTRAMULSION™ dispersions. This trademark is the property of Whitehill Oral Technologies, Inc. For further information regarding ULTRAMULSION™ dispersions, see copending application Ser. No. 08/144,778, now U.S. Pat. No. 5,538,667, the disclosure of which is hereby incorporated herein by reference. See also copending patent application Ser. Nos. 08/462,613; 08/462,600; 08/463,010; 08/461,698; 08/464,403; 08/462,599; and 08/462,930; all filed on Jun. 5, 1996, the disclosures of which are hereby incorporated by reference.

The ULTRAMULSION™ dispersion based oral care products of the present invention exhibit unique and unexpected substantivity to oral surfaces including teeth and gums while providing a reservoir for various lipid soluble active ingredients resulting in antiplaque, antibacterial, antigingivitis benefits that last for extended periods. This combination of enhanced substantivity and the reservoir effect described in detail below are further combined with excellent particle size to provide optimum coatings to the oral cavity.

Oral care products containing the ULTRAMULSION™ dispersions of the present invention include: rinses, spray, gels, creams, toothpastes, tooth powders, denture cleaning tablets, dental floss, interproximal simulators, mints, chewing gums, pet treats and pet main meals.

The compositions of the present invention may be used by dentists and hygienists in various professional oral hygiene treatment and/or may be used by consumers in various at-home and away-from-home oral hygiene products ranging from mouth rinses, gels, toothpastes, tooth powders, dental creams, denture wearers products, dental floss, to interproximal simulators, mints and chewing gums and sprays respectively.

As to Antiplaque Benefits

The present invention further relates to the interference with the formation of plaque. Plaque is a microbial coating on tooth surfaces, bound together by natural polymers (e.g., mucopolysaccharides) formed by microbial action on the cell debris, food remnants, sugars and starches in the mouth. Embedded in this polymer matrix are the bacteria normal to the oral cavity but, when trapped against tooth surfaces and protected by the matrix from easy removal, are in excellent position for "mischief." Most dental texts implicate plaque in the formation of caries, or tooth decay. In addition, these embedded bacteria release toxins that cause gingivitis, bleeding and swelling of the gums. Gingivitis can lead to periodontitis in which gums recede, pockets of infection form and teeth loosen.

Plaque formation is an ongoing process. Various gel and paste dentifrice preparations, mouth rinse and mouth pre-rinse preparations make plaque and/or tartar control claims. One disadvantage of these preparations is that only a relatively short time during which the teeth are being cleaned or the mouth is being rinsed is available for these preparations to take effect. These preparations generally have little residual effect on plaque formation. Additionally, some of these preparations such as mouth rinses and pre-rinses contain various antimicrobial substances which may alter the critically balanced microflora of the mouth. Another disadvantage of these preparations is the general infrequency of use. That is, most are used once or perhaps twice daily and seldom when they are most needed, e.g., after meals, snacks, smoking, drinking, coffee breaks, etc.

Effective oral hygiene requires that three control elements be maintained by the individual:

1. Physical Removal of Stains, Plaque and Tartar.

This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.

2. Surfactant Cleansing.

This is required to remove: food debris and staining substances before they adhere to the tooth surfaces; normal dead cellular (epithelial) material which is continually sloughed off from the surfaces of the oral cavity and microbial degradation products derived from all of the above. Besides the obvious hygienic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth.

3. Frequency of Cleansing.

This is perhaps the most difficult to provide in today's fast-paced work and social environment. Most people recognize that their teeth should be brushed at least 3 times a day plus after each snacking occasion.

The simple fact is that most of the population brush once a day, some brush morning and evening, but precious few carry toothbrush and dentifrice to use the other three or four times a day for optimal oral hygiene. Consumer research suggests that the population brushes an average of 1.2 times a day. Thus, the 24 hour period between brushings for a majority of the population provides optimum plaque forming conditions with no interruptions.

Since plaque is regarded by most of the dental profession as a causative agent leading to various dental pathologies as noted above, there is considerable desire by most consumers to disrupt or prevent the formation of plaque on a daily basis. There are three oral care strategies which address the problem of plaque: abrasion, anti-microbial agents and removal of precursors to plaque.

1. Abrasive removal of the plaque film, once it has firmly adhered to the tooth surface, is the only totally effective cleansing mechanism. Again, professional dental hygiene is the most effective, but recently a number of special abrasive toothpastes have been accepted by dental organizations as partially removing adhered plaque and the tartar which subsequently forms from the plaque.

2. Antimicrobial action could affect plaque formation in two ways, (a) reducing the number of bacteria in the mouth which form the mucopolysaccharides and (b) killing those bacteria trapped in the film to prevent further growth and metabolism. However, the medical and dental community is divided about the advisability of frequent use of antimicrobial agents in the mouth in rinses or pre-rinses, especially the most effective ones, except under strict supervision of licensed practitioners. There are a number of reasons given, but one concern is that such materials would upset the ecological balance of the mouth. A balanced, "friendly" microbial population is necessary to prevent pathogenic organisms from taking over.

3. Removal of plaque precursors requires the reduction of food sources and building blocks required for the bacteria to synthesize the mucopolysaccharides which polymerize into the plaque film. Going far back into the chain of events leading to plaque formation and interrupting the chain has much to commend it as a sound oral hygiene strategy. However, for this strategy to be effective, the plaque building blocks must be interrupted periodically. As noted above, heretofore, the oral hygiene preparations described above fall short on "frequency-of-use" basis.

For reference see: L. Menaker, The Biologic Basis of Dental Caries, Chapters 5, 11, 12, 14, 16 and 18, Harper & Row (1980). See also U.S. Pat. Nos. 4,465,661; 3,507,955; 4,902,497; 4,661,341; 4,666,708; 4,537,778; 4,657,758; 3,624,120; 4,525,342; 4,476,107; 5,078,988; 2,806,814; 4,774,077; 4,612,191; 4,353,890; 4,894,220; British Patent No. 689,679, Gatter et al., *Journal of Pharmaceutical Sciences*, 74: 1228–1232 (1985); and Bass, *Dent. Items of Interest*, 70: 921–34 (1948).

As to Antitartar Benefits

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature calculus deposits are regarded by many as a constant source of mechanical irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium. The prior art discloses a number of chelating agents for this purpose. British Pat. No. 490,384, Feb. 15, 1937, discloses oral compositions containing ethylenediaminetetraacetic acid (EDTA), nitrilotriacetic acid and related compounds as anticalculus agents. U.S. Pat. No. 3,678,154, Jul. 18, 1972 to Widder et al. discloses oral compositions containing certain polyphosphonates and fluoride.

U.S. Pat. No. 3,737,533, Jun. 5, 1973 to Francis discloses oral compositions containing certain carbonyl diphosphonates. In addition to the above references, the prior art discloses dentifrices and mouthwashes containing soluble pyrophosphate salts which have been included for a variety of purposes. Included among such references are U.S. Pat. No. 2,941,926, Jun. 21, 1960 to Salzmann et al. which discloses dental powders containing chlorophyll and pyrophosphate salts. U.S. Pat. No. 3,137,632, Jun. 16, 1964 to Schiraldi discloses toothpastes containing pyrophosphate salts. U.S. Pat. Nos. 3,927,201 and 202, Dec. 16, 1975 to Baines et al. and Harvey et al., respectively, disclose toothpastes which utilize soluble pyrophosphates as abrasives. U.S. Pat. Nos. 4,244,931, Jan. 13, 1981 and 4,247,526, Jan. 27, 1981 to Jarvis et al. disclose pyrophosphate salts in dicalcium phosphate systems. Jap. Patent Application Disclosure No. 4945-1974 discloses soluble pyrophosphates in a variety of dentifrice systems. U.S. Pat. No. 4,333,551, Apr. 6, 1982 to Parran discloses tetralkali metal salts in mouthwash compositions.

In addition to the use of the above mentioned materials the use of certain acrylic acid polymers and other agents have also been disclosed for use as anticalculus agents. Included among such agents are polyelectrolytes such as copolymers of maleic anhydride and ethylene disclosed in U.S. Pat. No. 3,429,963, Feb. 25, 1969 to Shedlovsky. Shedlovsky also discloses polyacrylic acid having an average molecular weight of 1500 and greater. Other references disclosing polyacrylic acids in oral compositions are South African Pat. No. 720898, Sep. 12, 1972 which discloses such acids having a molecular weight of from 1000 to 2,000,000; and U.S. Pat. No. 4,304,766, Dec. 8, 1971 to Chang discloses polyacrylic acid having a molecular weight in the range of 2,000 to 4,000,000 for use as a membrane to prevent the elution from teeth of previously applied agents. Finally U.S. Pat. No. 3,956,480, May 11, 1976 discloses complexes of anionic polymers (e.g., acrylic acid) and a cationic therapeutic agent (e.g., chlorhexidine) as anticalculus agents.

As to Anti-Gingivitis Benefits

It is generally accepted that antimicrobial substances are most effective in responding to gingivitis flare ups/infections of the gums. Suitable antimicrobials include stannous fluoride, as described in: U.S. Pat. Nos. 5,057,308; 5,057,309; 5,057,310 and in the FDA filing responsive to the Sep. 9, 1990 call-for-data (55 Fed. Reg. 38560) filed by WhiteHill Oral Technologies Jun. 6, 1991, Docket 81N-0033, OTC 210246 to 210262 and 210339 and specifically the "Annotated Bibliography set out in Vol. VI of said filing.

Other anti-gingivitis antimicrobials include chlorhexidine, halogenated diphenyl ethers such as triclosan, phenol and its homologs and the essential oils used in Listerine®. U.S. Pat. Nos. 4,022,880 & 4,894,220 disclose and claim various triclosan based oral care products. U.S. Pat. No. 4,894,220 includes an extensive teaching on phenol and its homologs suitable as antimicrobial agents. Metronidazole is discussed in detail in U.S. Pat. No. 4,568,535. The Listerine® essential oils are described in detail by Kornman in *Journal of Periodontal Research*, Supplement 1986: 5–22 (1986).

Other Anti-Plaque Active Ingredients Include a. Quaternary ammonium compounds including benzethonium chloride, cetylpyridinium chloride as described by Volpe et al., *Journal of Dental Research*, 48: 832–841 (1969) and Gjermo et al., *Journal of Periodontal Research*, 5: 102–109 (1970).

b. Phenolic compounds including the mixture of thymol, eucalyptol, menthol along with methyl salicylate described as "essentials oils" in Listerine®. See Fornell et al., *Scan-* dinavian *Journal of Dental Research*, 83: 18–25 (1975), Lusk et al., *Journal of the American Society of Preventive Dentistry*, 4: 31–37 (1974); Gomer et al., *Journal of the American Society of Preventive Dentistry*, 2: 12–14 (1972).

As to Periodontitis Benefits

The main cause of tooth loss in adults is periodontal disease. Yet, surprisingly, less than one percent of the public expenditures for dental treatment is for periodontal disease (see *J. Dent. Educ.*, 43: 320 (1979). This is because conventional periodontal treatment is too expensive for most individuals, mainly due to the labor intensive, symptomatic treatment that is usually performed by highly skilled specialists.

Periodontal disease is an all-inclusive term for a variety of clinical entities that are forms of either gingivitis or periodontitis. Gingivitis is an inflammation of the gingiva or gums that can be associated with poor oral hygiene and/or hormonal states of the host. It is assumed, but not proven in the human, that gingivitis will progress to periodontitis, which is the form of the disease in which the infection has progressed to involve the oral tissues which retain the teeth in the jaw bone. Periodontitis is the more severe form of the disease, and if untreated, will eventuate in the loss of the tooth.

Dentists have long assumed that periodontal disease originates by the overgrowth of bacteria on the tooth surfaces in aggregates known as dental plaque. If this plaque persists for long periods of time on the tooth surfaces, it may in some instances calcify, forming the hard substance known as calculus. Numerous studies describe chemical agents which can in vitro and in vivo reduce plaque formation and calculus. However, none of these chemical agents has been reported to be successful in treating periodontitis.

A substantial number of different types of compounds and compositions have been developed for use as antibacterial and antiplaque agents, e.g., benzethonium chloride and cetyl pyridinium chloride, disclosed in U.S. Pat. No. 4,110,429, or as anticalculus agents, e.g., 2-phosphono-butane 1,2,4-tricarboxylic acid, disclosed in U.S. Pat. No. 4,224,308. These compounds are designed to be used by the individual in dentifrices, dental powders, pastes, mouthwashes, non-abrasive gels, chewing gums, topical solutions and the like, e.g., see U.S. Pat. No. 4,205,061. They are designed to be used as prophylactic agents, usually without requiring a prescription or supervision during usage, e.g., see U.S. Pat. No. 4,251,507. Often they are compounded with detergents and other cleaning agents, and this cleaning action is often an important aspect of the invention, e.g., see U.S. Pat. Nos. 4,251,507 and 4,205,061. None of these compounds or compositions are designed to be used as antimicrobial agents for the treatment of periodontitis, nor are they formulated to be slow release devices for these antimicrobial agents in vivo.

Recent research in periodontal disease (see, for example, Chemotherapy of Dental Plaque Infections, *Oral Sci. Rev.*, 9: 65–107 (1976) indicates that gingivitis and periodontitis are characterized by different types of bacteria. Gingivitis is associated with the accumulation of gram positive cocci and actinomyces, whereas periodontitis is characterized by proportional increases in anaerobic bacteria, such as spirochetes and black pigmented bacteroides (see "Host-Parasite Interactions in Periodontal Disease," R. J. Genco and S. E. Mergenhagen, eds. Amer. Soc. for Microbiol. Washington, D.C. p. 27–45, 62–75, 1982). The different bacterial compositions of plaque associated with either gingivitis or periodontitis suggest that a mode of treatment that is effective in gingivitis may not be effective in periodontitis. Previous discoveries in the area of periodontal disease have assumed that there is no bacterial specificity in periodontal disease. This is now known to be incorrect. These bacterial differences in plaque may explain why an agent effective in plaque control, such as chlorhexidine, has little effect on gingivitis and no published effect on periodontitis.

Another important finding from recent periodontal research is that the composition of the dental plaque will differ according to its location on the tooth surface. Above the gingival or gum margin, facultative bacteria, such as gram positive cocci and rods, are numerically dominant, whereas below the gum margin, anaerobic motile bacteria such as spirochetes, and anaerobic gram negative rods including the black-pigmented bacteroides are predominant. In other words, two different microbial ecosystems are present on the same tooth surface.

A preferred antimicrobial agent for the treatment of periodontal diseases is metronidazole. See U.S. Pat. No. 4,568,535 and Soskolne et al., *J. Perio. Res.*, 18: 330–336.

Periodontal disease is a condition caused by a pathogenic microbial ecology established within the gingival sulcus which deepens to become a periodontal pocket. This microbial ecology, located deep within the periodontal pocket, differs greatly from that of the superficial oral environment by being more anaerobic, having a larger number of Gram negative organisms, and having a greater proportion of motile species.

Several factors impede the diffusion of medicinal agents when applied to the superficial periodontal tissues. Anatomically, the gum tissue is closely adapted to the neck of the teeth, mechanically restricting the diffusional pathway. In addition, a fluid termed gingival crevice fluid, with the approximate composition of plasma, permeates the periodontal environment and is continually produced by the diseased periodontal tissues at a rate of 10 to 100 microliters per hour. This fluid, emanating from the diseased pocket lining, creates a net outward flow further impeding the introduction of medications from superficially applied drug delivery devices. These interferences are sufficiently effective to insulate the pocket environment to the extent that saliva does not penetrate, and topically applied medicinal agents have been found largely ineffectual in the treatment of established periodontitis.

Although mouth rinses may be effective in the reduction of superficial gingivitis resulting from poor home care procedures, the effective radius of action of these agents does not extend to the periodontal pocket. Introduction of antibacterial agents in solution form into the periodontal pocket is similarly ineffective due to the rapid clearance of such agents so that the duration of contact at the active site is minimal.

Conventional therapy for periodontal disease, as first enunciated by Pierre Fauchard in 1746 in his book entitled "The Surgeon Dentist, a Treatise on Teeth," involves the mechanical removal of bacterial plaques and accumulations from the periodontal pocket at periodic intervals. This may include periodontal surgery to achieve access and to recontour damaged tissues. These procedures require a high degree of technical expertise from the practitioners of the art, are expensive, and often result in pain, extensive bleeding, and general discomfort on the part of the patient so treated. Since these procedures provide, at best, only temporary reduction in bacterial populations, they must be repeated at regular intervals to be effective. As discussed by Lindhe and coworkers in "Healing Following Surgical/Non-Surgical Treatment of Periodontal Disease" in the *Journal of Clinical Periodontology*, Vol. 9, pages 115–128, the frequency of repetition needed for optimal results may be as high as once every two weeks.

Methods for administering drugs for periodontal therapy have heretofore largely been concerned with superficial application. For example, long-acting capsules or tablets held in the mouth (see U.S. Pat. No. 3,911,099); buccal implants for releasing drugs into the saliva (see U.S. Pat. No. 4,020,558); topically applied gels (see U.S. Pat. No. 3,679,360); topically applied drug-containing bandages (see U.S. Pat. No. 3,339,546); a drug-containing plastic hardenable mass (see U.S. Pat. No. 3,964,164); a medicated periodontal dressing (see U.S. Pat. No. 3,219,527); a topical dressing composed of a finely divided particulate carrier and suspended medicinal agents (see U.S. Pat. No. 3,698,392); a bandage for covering moist mucosal surfaces (see U.S. Pat. No. 3,339,546); a microencapsulated liquid droplet formation for topical application to the gums of dogs and other animals (see U.S. Pat. No. 4,329,333); and foam-film devices containing medication (see U.S. Pat. No. 3,844,286). In addition, several fibrous forms for superficial medication have been described, including impregnated or drug-releasing forms of dental floss (see U.S. Pat. Nos. 3,417,179, 2,667,443, 2,748,781, 3,942,539); solid absorbable fibers of polyglycolic acid with medicants incorporated therein (see U.S. Pat. No. 3,991,766); and cellulose acetate hollow fibers (see U.S. Pat. No. 4,175,326). See also U.S. Pat. No. 4,892,736.

All of the foregoing references and the references cited in these references are incorporated in the description of the present invention.

The ULTRAMULSION™ dispersions of the present invention are distinct from other emulsions as will become apparent from the following:

When a system consists of a single liquid phase it is described as a solution. A system containing two or more liquid phases is described as a multiphase solution or emulsion.

According to Becher, an emulsion is an unstable heterogeneous system in which the diameters of the dispersed droplets in general exceed 1000 Å. Becher P. in "Emulsions, Theory & Practice", (P. Becher, Ed.) page 2, Rheinhold, N.Y., 1965.

A more comprehensive definition of emulsion is advanced by Clayton: "An emulsion is a system containing two liquid phases, one of which is dispersed as globules in the other. The liquid which is broken up into globules is termed the dispersed or discontinuous phase, while the liquid surrounding the globules is known as the continuous phase or dispersing medium" Clayton, W., "The Theory of Emulsions and Their Technical Treatment", 4th Ed. page 1, the Blakiston Co., Philadelphia, 1943. It is well accepted that, mechanical work is required to affect such an emulsion, see Bancroft W. D., *J. Phys. Phy. Chem.*, 17: 501 (1913).

According to Prince, an emulsion may be defined as a dispersion of two (or more) mutually insoluble liquids, one in the other. Because of the surface tension forces at play between the two liquids, the dispersed phase consists of spherical droplets. Prince, L. M. in "Microemulsion Theory & Practice", pg. 2, Academic Press Inc., New York, NY (1977). See also Prince, L. M. in "Biological Horizons in Surface Science", pg. 361, Academic Press Inc. (1973).

Emulsions, are generally not stable and upon standing or after centrifuging tend to separate into two or more liquid layers.

The three definitions of emulsions set forth above share one common attribute, that is, mechanical work must be put into the emulsions described in order to disperse one liquid in the other in the form of droplets. This mechanical work can be in the form of agitation, homogenization, ultrasonication, etc.

In contrast, dispersions of very small droplet sizes which are formed spontaneously without the input of any mechanical work are called microemulsions. See Prince 1977, p. 3. Generally, two surfactants are used in forming microemulsions, i.e., a water soluble surfactant and a co-surfactant such as alcohol, where one phase of the microemulsion is generally water. Thus, dilution or adulteration of the dispersed phase by the co-solvent generally accompanies microemulsion formation. The ratio of surfactant to dispersed phase in microemulsions is much higher than that of emulsions. Microemulsions are further characterized as optically clear or opalescent and when spun in a laboratory centrifuge for 5 minutes at 100 G's, the dispersion remains stable and does not separate.

Thus, fine particle sizes, exceptional stability and rheological properties that can be easily adjusted, distinguish microemulsions from emulsions. Moreover, to date, no microemulsions have appeared in which one of the mutually insoluble liquids is not water. See Prince, page 34, (1977).

It has been surprisingly found that certain ULTRAMULSION™ dispersions, i.e., those of the present invention, provide various oral care products with improved antiplaque and antigingivitis, etc. performance attributed to: (a) their enhanced substantivity, (b) the reservoir effect achieved by solubilizing various lipid soluble active ingredients in the discontinuous silicone phase of the ultramulsion and (c) the generally small particle size of the dispersed silicone phase to effect suitable coatings in the oral cavity.

It is an object of the present invention to provide ULTRAMULSION™ dispersion based antiplaque, antitartar, antigingivitis and periodontal treatment products with enhanced substantivity while containing a reservoir of various active ingredients for treating various oral hygiene conditions.

It is another object of the invention to provide a method for manufacturing the ULTRAMULSION™ dispersion based oral care products of the invention.

It is yet another object of the invention to provide a method to treat various oral hygiene conditions with the ULTRAMULSION™ dispersions of the present invention.

It is another object of the present invention to provide ULTRAMULSION™ dispersion based oral care products with improved oral care coating properties.

It is also an object of this invention to provide an ULTRAMULSION™ dispersion for water based oral care products without the need to resort to use of complex high energy processes.

It is a further object of the present invention to provide ULTRAMULSION™ dispersion based oral care products wherein various lipid soluble and/or lipid dispersible actives are released from the ULTRAMULSION™ dispersion coating into the oral cavity over an extended period.

These and other objects will become readily apparent from the detailed description which follows.

Unless otherwise indicated, all percentages and ratios herein are by weight.

SUMMARY OF THE INVENTION

The ULTRAMULSION™ dispersions of oral care products of the present invention combine certain characteristics of emulsions with certain features of microemulsions. That is, like emulsions, they are two phase systems comprising a silicone dispersed in a continuous, surfactant phase, wherein the silicone is insoluble in the surfactant. Unlike emulsions, but like microemulsions, these dispersions are stable. Unlike microemulsions, but like emulsions, mechanical work is required to form ultramulsions. Unlike microemulsions, but like emulsions, these ULTRAMULSION™ dispersions are not formed spontaneously. Like emulsions, the ULTRAMULSION™ dispersions do not contain a cosolvent commonly found in microemulsions. Of course, the ULTRAMULSION™ dispersions of the present invention can be dispersed in various liquids such as water as stable dispersions. These ULTRAMULSION™ dispersions have excellent utility in various oral care products. See various examples below and the various tables below.

While not wishing to be bound by theory, it is hypothesized that unlike either emulsions or microemulsions, the dispersed silicones of the ULTRAMULSION™ dispersions of the present invention are uniquely oriented with their polar moieties in one general plane and their hydrophilic moieties in a plane approximately opposite that of the polar moieties. This orientation promotes stability as well as bonding between the polar or hydrophilic moieties and various surfaces in the oral cavity thereby effecting oriented, monolayer coatings of the silicone onto these surfaces. These oriented dispersions of silicones have a surprising broad range of utility in oral care as detailed in the various examples below. This orienting is illustrated in FIGS. 1 & 2.

Figure 1:
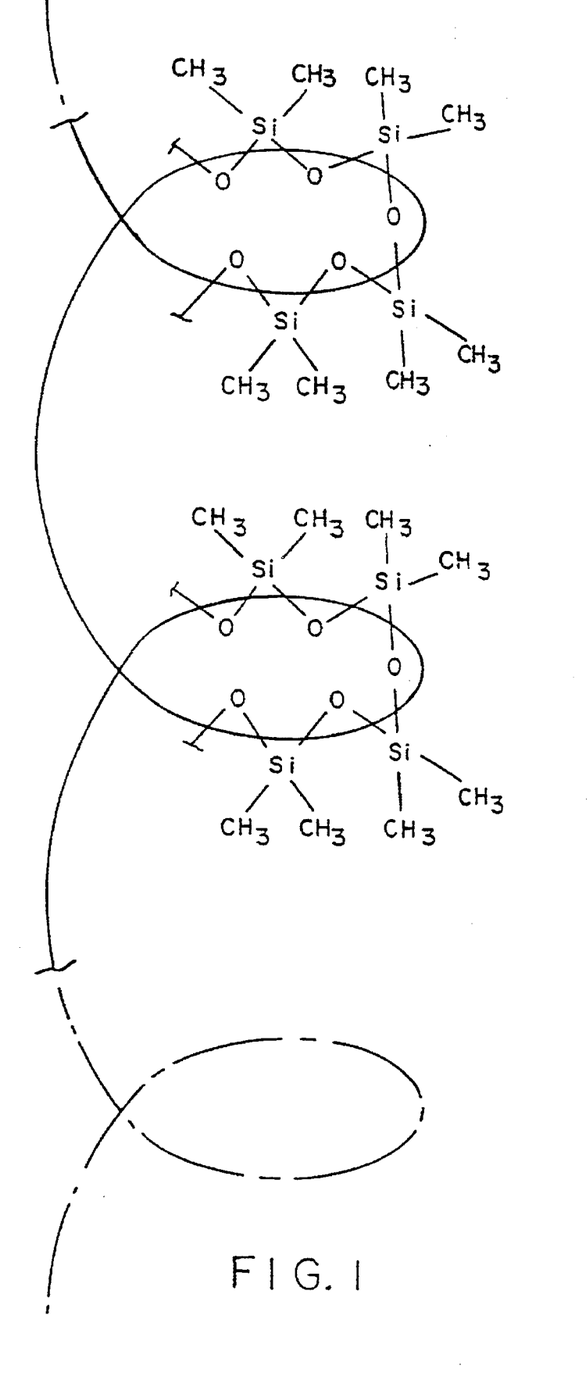
FIG. 1 illustrates the "coiled" molecular configuration proposed to polydimethylsiloxanes.
Figure 2:
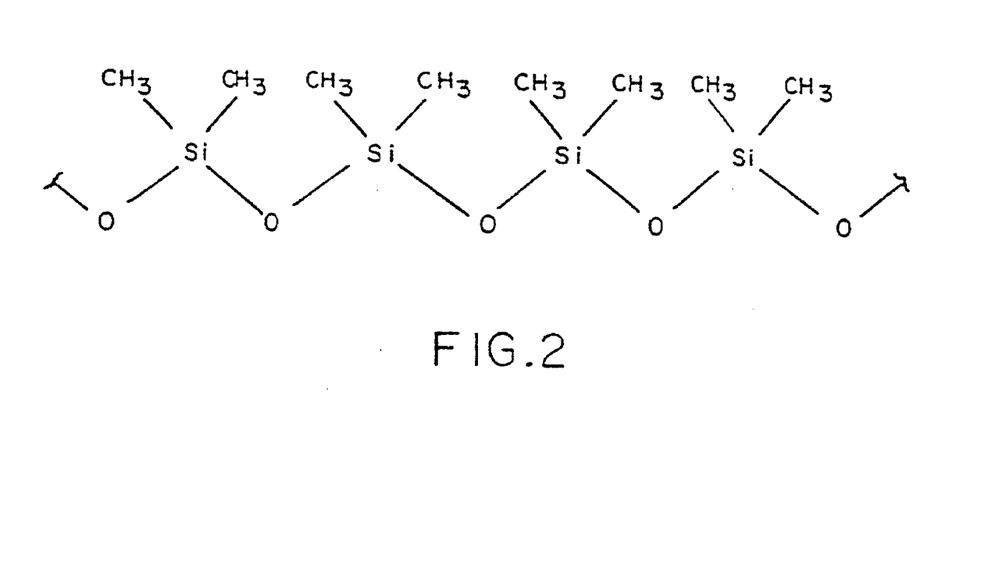
FIG. 2 illustrates the proposed molecular configuration of oriented polydimethylsiloxanes after ULTRAMULSION™ dispersion processing.

The emulsifying effects of uncoiling of the silicone molecule with the oxygen moieties generally oriented in one plane distinct from that of the organo moieties as illustrated in FIGS. 1 and 2, are further substantiated by the following references: Eur. Poly. J., 26: 654 (1990); J. Chem. Phys., 49: 1398 (1965); J. Chem. Phys., 54: 5011 (1971); J. Chem. Phys., 59: 3825 (1973); Macromolecules, 7: 229 (1974); Macromolecules, 11: 627 (1978) and "Rubber-Like Elasticity: A Molecular Primer," J. Mark, New York, Wiley-Interscience, 1988.

Methods of preparing polyorganosiloxane emulsions with an average particle size of less than about 0.3 microns and polyorganosiloxane microemulsions with an average particle size of less than about 0.14 micron are described in U.S. Pat. No. 4,620,878. Preparation of oil-in-water microemulsions are described in U.S. Pat. No. 4,146,499. Specific surface active compositions used as emulsifiers with diorganopolysiloxanes to form transparent microemulsions are described in U.S. Pat. Nos. 4,0562,331 and 3,975,294. U.S. Pat. No. 3,433,780 teaches the preparation of colloid silane suspensions. See also "Chemistry and Technology of Silicones," W. Noll, pp. 428 to 431 (1968); Journal of Society of Cosmetic Chemists, 25: 609–619 (1974) and Journal of Colloid & Interface Science, 44: 242–248 (1973).

Miceliar dispersions, microemulsions, transparent emulsions are described in detail in "Annals of the New York Academy of Science," Shulman & Montagne (1961); U.S. Pat. No. 2,356,205, "The Theory of Emulsions & Their Technical Treatment," 5th Edition, 1954, U.S. Pat. Nos. 3,497,006; 3,506,070, 3,254,714 and 3,307,628.

The aqueous-free ULTRAMULSION™ dispersions of silicones in surfactants as described herein are neither taught nor suggested by the foregoing references.

DETAILED DESCRIPTION OF THE PREFERRED EMBODIMENTS

Referring to the drawings, FIG. 1 illustrates the accepted "coiled" configuration advanced for polydimethylsiloxanes, wherein the methyl moieties are oriented outward while the oxygen moieties are oriented inward towards the axis of the coil or helix. This configuration does not readily promote "bonding" between the oxygen moieties and compatible surfaces such as those in the oral cavity.

FIG. 2 illustrates the "uncoiled oriented" configuration proposed for polydimethylsiloxanes that have been dispersed in the stable, ULTRAMULSION™ dispersion of the present invention, wherein the oxygen moieties are generally oriented in one plane distinct from that of the methyl moieties. This proposed uncoiled oriented configuration appears to support the unique and unexpected stability "bonding and enhanced substantivity" properties of the ULTRAMULSION™ dispersion of the present invention, as evidenced by the various coating applications of these ULTRAMULSION™ dispersions to surfaces in the oral cavity. See examples below.

Figure 3:
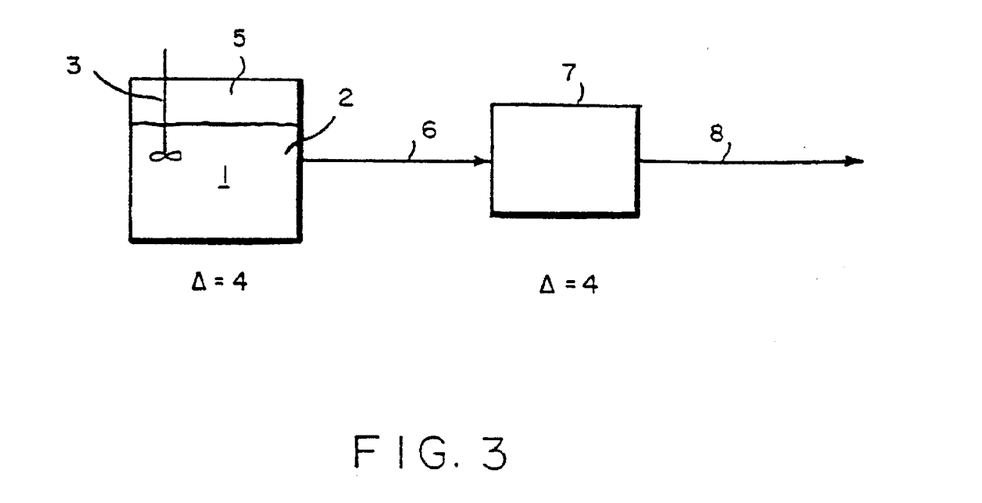
FIG. 3 illustrates schematically an ULTRAMULSION™ dispersion process of the invention.

FIG. 3 illustrates the ULTRAMULSION™ dispersion process of the present invention wherein a nonionic surfactant and a polydimethylsiloxane 1, substantially free from water and co-solvent, are mixed in vessel 2, provided with mixing means 3, heat source 4, and inert head space 5. The heated and mixed surfactant and poly-dimethylsiloxane 6, is then subjected to high shear dispersion at an elevated temperature in dispersing means 7, to produce the ULTRAMULSION™ dispersion 8, of the invention.

Figure 4:
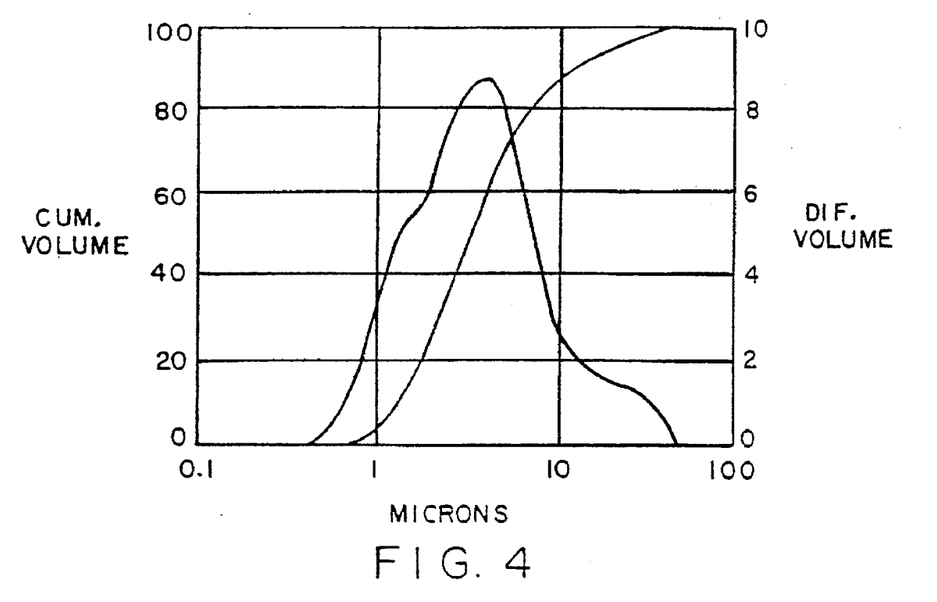
FIGS. 4 and 5 illustrate that the ULTRAMULSION™ dispersions of the invention produced via various high shear dispersing means having particle size distribution of 80+% under 10 microns.

FIG. 4 is a chart describing the particle size distribution of an ULTRAMULSION™ dispersion of the invention containing 95–5% by weight nonionic surfactant and 5–50% by weight polydimethylsiloxane (2.5 million cs) produced in a continuous process with an IKA Work dispersing means, (high shear dispersing) with an inlet temperature of 140° C. and an outlet temperature of 210° C.

Figure 5:
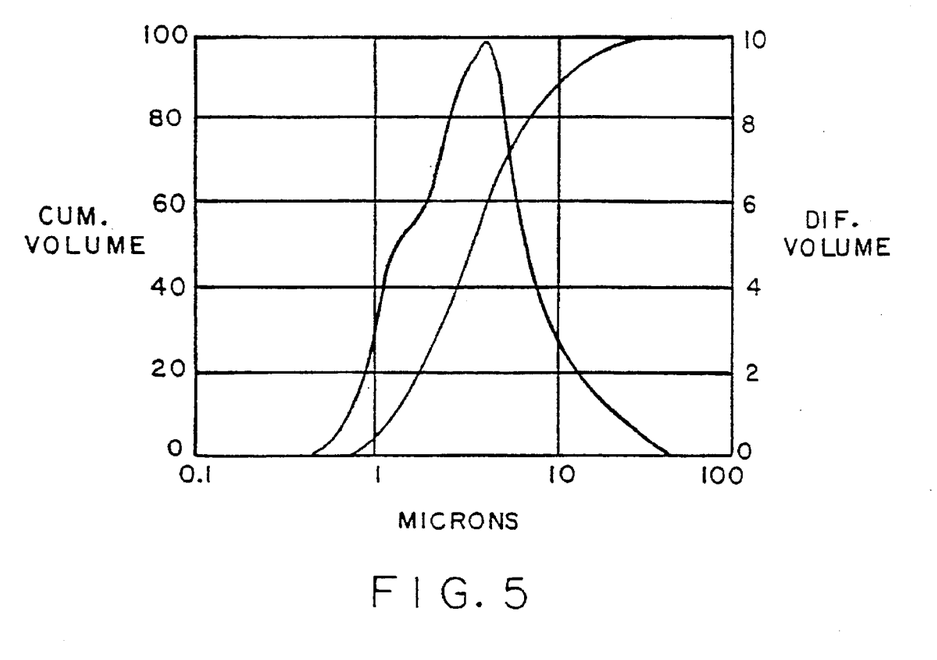

FIG. 5 is a chart describing the particle size distribution of an ULTRAMULSION™ dispersion of the invention containing 95–50% by weight nonionic surfactant and 5–50% by weight polydimethylsiloxane (2.5 million cs) produced in a batch process with a Ross M/E 100 LC dispersing means fitted with a 20 mesh screen, operated at a temperature from 120° to 160° C.

Figure 6:
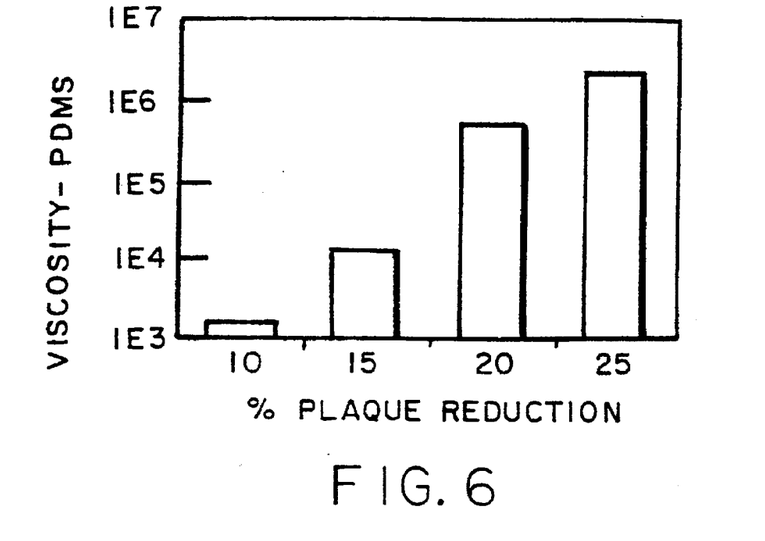
FIGS. 6 and 7 are a graph and a chart respectively showing the effect of increased silicone viscosity on plaque building in a certain oral care product.
Figure 7:
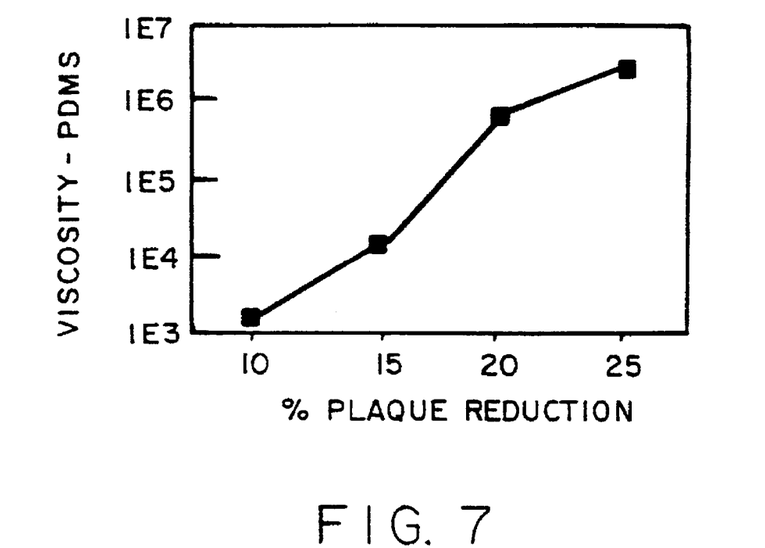

FIGS. 6 and 7 disclose the influence of increasing viscosity of the silicone in the ULTRAMULSION™ dispersion on the anti-plaque effect of this ULTRAMULSION™ dispersion when introduced into the oral cavity several times throughout the day as a mint. This reduction in plaque buildup is a substantial advance in establishing the efficacy and value of away-from-home oral care products such as mints.

The ULTRAMULSION™ dispersions of the present invention can be included in traditional oral care products such as rinses, toothpastes, gels etc. to enhance the anti-plaque, anti-tartar and/or anti-gingivitis performance of such products as described in detail in the examples below.

These same ULTRAMULSION™ dispersions can further contain various lipid soluble active ingredients in the dispersed silicone phase and thereby impart extended anti-plaque, anti-tartar, anti-gingivitis and/or anti-periodontia effects to various rinses, toothpastes etc. This "reservoir" effect of silicones containing active ingredients was documented with triclosan containing toothpaste by Rolla et al., in clinical studies reported in *Scand. J. Dent. Res.*, 101: 130–138.

The ULTRAMULSION™ dispersion can contain various agents found to be effective in treating periodontal pockets such as metronidazole, antibiotics such as tetracycline and penicillin and mixtures of such pathogen specific substances as described by Genco in *J. Periodontology*, 52: 545–558 (1981) and U.S. Pat. No. 4,892,736 and "Medical Applications of Controlled Release", CRC Press, Boca Raton 1984.

Heretofore these periodontal pockets were fitted with "slow release" films etc. containing antimicrobials and/or antibiotics etc. such as described by Goodson in U.S. Pat. No. 4,892,736 and Loesche in U.S. Pat. No. 4,568,535 and the pocket then "packed" with a periodontal dressing. It is suggested these perio-pockets can be treated with gels containing the ULTRAMULSION™ dispersions of the present invention wherein the silicone dispersed phase contains the active ingredient and releases the active ingredient from the silicone reservoir into the perio pocket. These gels would "fill" the pocket with the pocket "dressed" as described by U.S. Pat. No. 4,892,736. See also U.S. Pat. Nos. 4,981,693 and 4,933,182.

For purposes of the present invention, the term silicone means a clear, colorless substance containing polydialkylsiloxane polymers with average kinematic viscosities ranging from about 100,000 centistokes (cs) to about 50 million cs, preferably from about 1 million cs to about 25 million cs, more preferably from about 1.5 million cs to about 10 million cs, and most preferably from about 2 million to about 5 million cs. This definition intentionally includes the so-called "gum" silicones having viscosities of 30 to 50 million cs. Certain high viscosity polydimethylsiloxane having viscosities from about 2.5 million cs to about 4 million cs are particularly preferred for the hair care products of the present invention. Other polydimethylsiloxanes suitable for the present invention include "substituted" water insoluble silicones and mixtures of polydiorganosiloxanes and substituted water insoluble silicones. Specifically, water soluble silicones are excluded from the ULTRAMULSION™ dispersions of the present invention.

The viscosity of some silicones can be measured by means of a glass capillary viscometer as set forth in Dow Corning Corporate Test Method CTM0004, Jul. 20, 1970.

The silicone fluid may be either a high viscosity polyalkyl siloxane as described in detail below. Mixtures of various silicones may also be used and are preferred in certain embodiments of the invention.

The polyether siloxane copolymer that may be used is, for example, a polypropylene oxide modified dimethylpolysiloxane although ethylene oxide or mixtures of ethylene oxide and propylene oxide may also be used.

References disclosing suitable silicone fluids include U.S. Pat. No. 2,826,551 to Green; U.S. Pat. No. 3,964,500 to Drakoff; U.S. Pat. No. 4,364,837 to Padher and British Pat. No. 849,433 to Woolston. All of these patents are hereby incorporated herein by reference. Also incorporated herein by reference is *Silicon Compounds* distributed by Petrarch Systems, Inc., 1984. This reference provides a very good listing of suitable silicone materials.

Silicone materials found especially useful in the present compositions to provide good oral hygiene results are silicone gums. Silicone gums described by Petrarch and others including U.S. Pat. No. 4,152,416, May 1, 1979 to Spitzer et al., and Noll, Walter, *Chemistry and Technology of Silicones*, New York, Academic Press 1968. Also describing silicone gums are various General Electric Silicone Rubber Product Data Sheets. All of these described references are incorporated herein by reference. "Silicone gum" materials denote high molecular weight polydiorganosiloxanes having a viscosity up to about 50 million cs. Specific examples include polydimethylsiloxane, polydimethylsiloxane, methylvinylsiloxane, copolymer, poly(dimethylsiloxane, diphenyl, methylvinylsiloxane copolymer and mixtures thereof.

As noted above high viscosity polydimethylsiloxanes i.e., those above 100,000 cs are preferred. Particularly preferred are polydimethylsiloxanes from between about 2.5 million cs and about 50 million cs. The safety of polydimethylsiloxanes for use in these various products is well documented. See Rowe et al., *Journal of Industrial Hygiene*, 30: 332–352 (1948). See also Calandra et al., "ACS Polymer Preprints", 17: 1–4 (1976) and Kennedy et al., *J. Toxicol & Environmental Health*, 1: 909–920 (1976).

As noted above, preferred polydimethylsiloxanes useful in the oral care compositions of the present invention are described as polymethylsiloxanes with the chemical composition:

wherein n is a whole number. These polydimethylsiloxanes have viscosities up to 50 million cs and are generally described as having high molecular weights.

The particle size of the silicone in the ULTRAMULSION™ dispersion of the present invention can range from between about 0.1 and about 10 microns. In a preferred embodiment of the present invention the particle size of polydimethylsiloxanes in the ULTRAMULSION™ dispersion ranges from between about 1 and about 5 microns. The particle size distribution of the polydimethylsiloxanes in the ULTRAMULSION™ dispersion of the present invention generally range from between about 80 and about 95% of the particles under 10 microns. See FIGS. 4 and 5. In a preferred embodiment of the present invention, from between about 80 and about 95% of the particles are under 5 microns. See also Table 2.

An essential component of the ULTRAMULSION™ dispersion is a surfactant. The surfactant, may be selected from any of a wide variety of synthetic anionic, amphoteric, zwitterionic and nonionic surfactants, that are safe for use in the oral cavity.

The surfactants suitable for the purposes of the present invention must function as the continuous phase and contain the disposal discontinuous silicone phase. Generally, these surfactants are liquid or meltable substances and include mixtures of surfactants as detailed in the examples and tables below.

Synthetic anionic surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxyl, sulfonate, sulfate, phosphate, or phosphonate. A general formula for these compounds is:

wherein $R^2$ contains an alkyl, alkenyl, or hydroxyl alkyl radical of from about 8 to 18 carbon atoms, from 0 to about 10 ethylene oxide moieties and from 0 to 1 glyceryl moiety; Y is selected from the group consisting of nitrogen, phosphorous, and sulfur atoms; $R^3$ is an alkyl or monohydroxyalkyl group containing 1 to about 3 carbon atoms; X is 1 when Y is a sulfur atom and 2 when Y is a nitrogen or phosphorous atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:

4-[N, N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphate;

3-[N,N-dimethyl-N-hexadecylammonio-propane-1-sulfonate;

4-[N,N-di(2-hydroxyethyl)-N-(2-hydroxydodecyl) ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and 5-(N,N-di(3-hydroxypropyl)-N-hexadecylammonio]2-hydroxypentane-1-sulfate.

Other zwitterionics such as betaines are also useful in the present invention. Examples of betaines useful herein include the higher alkyl betaines such as cocodimethyl carboxymethyl betaine, lauryl dimethyl carboxymethyl betaine, lauryl dimethyl alpha-carboxyethylene betaine, cetyl dimethyl carboxymethyl betaine, lauryl bis-(2-hydroxy-ethyl)carboxy methyl betaine, stearyl bis-(20-hydroxypropyl)-carboxymethyl betaine, oleyl dimethyl gamma-carboxypropyl betaine, lauryl bis-(2-hydroxypropyl)alpha-carboxyethyl betaine, etc. The sulfobetaines may be represented by cocodimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfo betaines, wherein the $RCONH(CH_2)_3$ radical is attached to the nitrogen atom of the betaine are also useful in this invention. The amido betaines are preferred for use in some of the compositions of this invention. A particularly preferred composition utilizes an amido betaine, a quaternary compound, a silicone, a suspending agent and has a pH of from about 2 to about 4.

Examples of amphoteric surfactants which can be used in the ULTRAMULSION™ dispersion of the present invention are those which can be broadly described as derivatives of aliphatic secondary and tertiary amine in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylamino-propionate, sodium 3-dodecylamino-propane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, disobutylene, octane, or nonane, for example.

2. Those derived from the condensation of ethylene oxide with the product resulting from the reaction of propylene oxide and ethylenediamine products which may be varied in composition depending upon the balance between the hydrophobic and hydrophilic elements which is desired. For example, compounds containing from about 40% to about 80% polyoxyethylene by weight and having a molecular weight of from about 5,000 to about 15,000 resulting from the reaction of ethylene oxide groups with a hydrophobic base constituted of the reaction product of ethylene diamine and excess propylene oxide, said base having a molecular weight of the order of 2,500 to 3,000 are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_2$ contains from 1 to about 3 carbon atoms and from 0 to about 1 hydroxy group, e.g., methyl, ethyl, propyl, hydroxy ethyl, or hydroxypropyl radicals. The arrow in the formula is a conventional representation of a semipolar bond. Example of amine oxides suitable for use in this invention include dimethyl-dodecylamine oxide, oleyldi(2-hydroxy-ethyl)amine oxide, dimethyloctylamine oxide, dimethyldecylamine oxide, dimethyltetradecylamine oxide, 3,6,9-trioxaheptadecyldiethylamine oxide, di)2-hydroxyethyl)-tetracylamine oxide, 2-dodecoxyethyldimethylamine oxide, 3-dodecoxy-2-hydroxypropyldi-(3-hydroxy-propyl)amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 18 carbon atoms in chain length from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyl-di(2-hydroxyl)-phosphine oxide, stearyldimethylphosphine oxide, cetylethylpropylphosphine oxide, cetyldiethylphosphine oxide, dodecyldiethylphosphine oxide, tetradecyl-diethylphosphine oxide, dodecyldipropylphosphine oxide, dodecyldi(2-hydroxyethyl)phosphine oxide, tetradecyl-methyl-2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophosphic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl menthyl sulfoxide, 2-ketotridecyl methyl sulfoxide, 3,6,9,-trioxooctadecyl 2-hydroxyethyl sulfoxide, dodecyl menthyl sulfoxide, oleyl 3-hydroxypropyl sulfoxide, tetradecyl menthyl sulfoxide, 3-methoxytridecyl methyl sulfoxide, 3-hydroxytridecyl methyl sulfoxide, 3-hydroxy-4-dodecoxy-butyl methyl sulfoxide.

Many additional nonsoap surfactants are described in McCUTCHEON'S, DETERGENTS AND EMULSIFIERS, 1979 ANNUAL, published by Allured Publishing Corporation which is incorporated herein by reference.

Particularly preferred nonionic surfactants are nonionic poloxamer surfactants of block copolymers of ethylene oxide and propylene oxide ranging from flowable liquids of varying viscosities, to paste, prills and cast solids with molecular weights from 1,100 to 150,000. Suitable nonionic surfactants are manufactured and marketed by BASF Corporation under the trademark Pluronic. Particularly preferred nonionic surfactants are Pluronic F-68, F-88, F-108 and Pluronic F-127. These are described in a BASF brochure entitled "Pluronic and Tetronic Block Copolymer Surfactant." These nonionic surfactants suitable for the present invention can be described by the following structure:

where x, y and x' are whole numbers. Surprisingly, the nonionic surfactants of choice for the ULTRAMULSION™ dispersion of the present invention are reported in the referenced brochure to have marginal detergency, emulsification and wetting properties. See Tables 1 and 2.

As noted above, the preferred nonionic poloxamer surfactants useful in the coating compositions of the present invention are described as polyoxyethylene-polyoxypropylene block copolymers such as Pluronic F-68, F-88, F-108 and F-127 (BASF) which have molecular weights of at least about 1000 such as described in U.S. Pat. Nos. 4,343,785, 4,465,663, 4,511,563 and 4,476,107, the disclosures of which are hereby incorporated herein by reference.

Emulsions of various coating substances including polydimethylsiloxanes in various surfactants including nonionic surfactants are disclosed and claimed in U.S. Pat. Nos. 4,911,927, 4,942,034; 4,950,479; 5,009,881; 5,032,387; 5,057,306; 5,057,307; 5,057,308, 5,057,309; 5,057,310, 5,098,711, 5,165,913 and 5,284,648. There is no teaching in these references that these highly viscosity silicone emulsions are stable nor that the "coating" substances are oriented as they are in the ULTRAMULSION™ dispersions of the present invention.

The ratio of surfactant to silicone in the ULTRAMULSION™ dispersion coating compositions of the present invention can range from between about 400:1 and about 1:2. In a preferred embodiment of the invention the ratio of surfactant to silicone is from between about 25:1 and 1:2. See Tables 1 and 2.

For the purposes of the present invention:

a. stable is defined as, dispersion of the ULTRAMULSION™ dispersion in water when subjected to centrifuging in a 100 G environment for 5 minutes, less than about 10% by weight of the ULTRAMULSION™ dispersion separates from the continuous water phase and/or a substantial portion of the dispersed phase resists separation. This latter definition is particularly applicable to higher viscosity silicones. See Table 2.

b. water-free means, that the ULTRAMULSION™ dispersion of silicone and surfactant is substantially free from water.

c. solvent free means, that the ULTRAMULSION™ dispersion of silicone and surfactant is substantially free from cosolvents such as ethanol, isopropanol, etc.

d. oriented means, that the polar moieties of the "uncoiled" polydimethylsiloxane in the ULTRAMULSION™ dispersion are generally aligned in one plane with the hydrophilic oil seeking moieties aligned in a second plane such as illustrated in FIG. 2.

e. monolayer means, that the monomolecular film of the ULTRAMULSION™ dispersion of the invention when dispersed in water is attracted to mucosa and hydroxyapatite by secondary bonding forces to form a substantive coating thereon.

The ULTRAMULSION™ dispersions of the present invention are prepared as follows:

Generally, if not a liquid, the surfactant is heated to a temperature at which it becomes a liquid. The silicone is dispersed in the heated surfactant with various high shear dispersing means.

Specifically the heated surfactant is mechanically stirred along with the silicone to form a pre-emulsion mixture in which the silicone is uniformly dispersed in the surfactant in droplets of a larger size then desired for the ULTRAMULSION™ dispersion but small enough to optimize the subsequent high shear dispersions. This mixture is subjected to high-shear dispersions with a means such as the IKA-WORKS DISPAX-Reactor with at least one superfine generator, alternatively, a Ross Model M.E., 100 LC fitted with a 20 mesh screen or a ultrasonicator such as MED-SONIC XL2010 fitted with 800-C Flow Cell & 800-21CT ¾ inch flanged horn can be used.

Various ULTRAMULSION™ dispersions which are prepared and analyzed are described in detail in the examples below.

TABLE I

ORAL CARE
% W/W

| Component | Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| Dimethicone viscosity-centistokes | | | | | | | | | | | |
| 100,000 | 10 | — | — | — | — | — | — | — | — | 33 | — |
| 600,000 | — | 10 | — | — | — | — | 33 | — | — | — | — |
| 2,500,000 | — | — | 10 | — | — | — | — | 33 | — | — | 10 |
| 4,000,000 | — | — | — | 10 | — | — | — | — | 33 | — | — |
| 30,000,000 | — | — | — | — | 10 | — | — | — | — | — | — |
| 50,000,000 | — | — | — | — | — | 10 | — | — | — | — | — |
| Poloxamer - 188 | — | — | — | — | — | — | — | — | — | 67 | — |
| Poloxamer - 238 | — | — | — | — | — | — | — | — | — | — | 90 |
| Poloxamer - 338 | 90 | 90 | 90 | 90 | 90 | 90 | — | — | — | — | — |
| Poloxamer - 407 | — | — | — | — | — | — | 67 | 67 | 67 | — | — |

Specific poloxamer/polydimethylsiloxane ULTRAMULSION™ dispersions suitable for use with various oral care products were prepared and analyzed as described in Table 2 below:

TABLE 2

ORAL CARE
% W/W

| | Example No. | | | | | | | | | |
|---|---|---|---|---|---|---|---|---|---|---|
| | 12 | 13 | 14 | 15 | 16 | 17 | 18 | 19 | 20 | 21 |
| Component | | | | | | | | | | |
| Dimethicone viscosity-centistokes | | | | | | | | | | |
| 600,000 | — | 11.6 | — | — | — | 10.0 | — | — | — | — |
| 2,500,000 | 10.0 | — | — | 11.9 | 11.9 | — | — | — | — | 14.0 |
| 4,000,000 | — | 11.6 | — | — | — | — | — | — | — | — |
| 30,000,000 | — | — | — | — | — | 11.6 | — | — | — | — |
| 50,000,000 | — | — | — | — | — | — | 11.6 | 10.0 | — | — |
| Lipid Soluble Component Mixture Of: | | | | | | | | | | |
| Thymol - 24% | | | | | | | | | | |
| Menthol - 16% | 10.0 | — | — | — | — | — | — | — | — | — |
| Eucalyptol - 36% | | | | | | | | | | |
| Methyl Salicylate - 24% | — | — | — | — | — | — | — | — | — | — |
| Stannous Fluoride | — | — | — | — | 1.75 | — | — | — | — | — |
| Triclosan | — | 1.16 | 1.16 | — | — | — | 1.16 | 1.16 | — | 2.0 |
| Chlorhexidine | — | — | — | — | — | — | — | — | — | — |
| Metronidazole | — | — | — | 1.3 | — | — | — | — | — | — |
| Benzocaine | — | — | — | — | 1.0 | — | — | — | — | — |
| Surfactant Poloxamer 338 | 80.0 | 97.24 | 87.24 | 86.8 | 87.25 | 89.0 | 87.24 | 87.24 | 80.0 | 84.0 |

The discontinuous silicone phase of the ULTRAMULSION™ dispersion can also contain a wide range of lipid soluble and/or lipid dispersible oral care active ingredients ranging from antimicrobials to desensitizing/substances, to healants such as aloe to vitamins such as vitamin E, to flavorants, etc. These various ingredients in the silicone phase of the ULTRAMULSION™ dispersion perform in various oral care products as though they are contained in a "reservoir" as they continue to be available at the ULTRAMULSION™ dispersion oral surface interface, as long as the ULTRAMULSION™ dispersion coating remains substantive to mouth surfaces. Similar effects attributed to this reservoir effect are described by Rölla et al., supra.

The oral care products containing the ULTRAMULSION™ dispersions of the present invention will contain a variety of essential components ranging from surfactants and abrasives for cleaning, to whiteners, to gelling aids to flavorants etc. These are detailed in various Examples described below.

Water is an essential component of most oral care products of the present invention which contain one or more of the various ULTRAMULSION™ dispersions described above. The water in these products is generally present at a level of from about 20% to about 95%, preferably from between about 60% and about 90%.

In addition these oral care products can contain a variety of nonessential optional components suitable for rendering such compositions more acceptable. See Tables 3 to 6 below.

Such conventional optional ingredients are well known to those skilled in the art, e.g., preservatives such as benzyl alcohol, methyl paraben, propyl paraben and imidiazolidinyl urea; cationic surfactants such as cetyl trimethylammonium chloride, lauryl trimethyl ammonium chloride, tricetyl methyl ammonium chloride, stearyldimethyl benzyl ammonium chloride, and di(partially hydrogenated tallow)-dimethylammonium chloride; thickeners and viscosity modifiers such as diethanolamide of a long chain fatty acid (e.g., PEG 3 lauramide), block polymers of ethylene oxide and propylene oxide such as Pluronic F88 offered by BASF Wyandotte, sodium chloride, sodium sulfate, polyvinyl alcohol, and ethyl alcohol; pH adjusting agents such as citric acid, succinic acid, phosphoric acid, sodium hydroxide, sodium carbonate, etc., perfumes; dyes; and, sequestering agents such as disodium ethylenediamine tetraacetate. Such agents generally are used individually at a level of from about 0.01% to about 10%, preferably from about 0.5% to about 5.0% by weight of the composition.

The ULTRAMULSION™ dispersions of the invention are particularly useful in compositions used by professionals to clean teeth. The inclusion of stannous fluoride in the discontinuous phase of the emulsion is particularly attractive as a means of treating interproximal caries. See Segueto et al., *Journal of Dental Research*, Vol. 10, No. 1, pp. 90–96, 1961 and Peterson et al., *Northwest Dentistry*, 276–278, September/October 1963.

The pH of the present compositions is preferably from 6 to 8.

Method of Manufacture

The various oral care products of the present invention can be made by mixing the materials together and heating if necessary and following accepted manufacturing practices for these various products as described in detail below.

Industrial Applicability

The products of the present invention have utility in a wide range of oral care products as illustrated below.

The examples set forth in Tables III through VII further describe and demonstrate preferred embodiments within the scope of the present invention. The examples are given solely for the purpose of illustration and are not to be construed as limitations of the present invention as many variations thereof are possible without departing from its spirit and scope.

TABLE III

TOOTHPASTE COMPOSITIONS % W/W

| Component | Example # | | | | | | | | | | | |
|---|---|---|---|---|---|---|---|---|---|---|---|---|
| | 22 | 23 | 24 | 25 | 26 | 27 | 28 | 29 | 30 | 31 | 32 | 33 |
| Dicalcium Phosphate Dihydrate | 49.0 | 49.0 | 49.0 | 49.0 | 49.0 | 49.0 | 49.0 | 49.0 | 49.0 | 49.0 | 49.0 | 49.0 |
| Sorbitol - 70% Aq. | 18.0 | 18.0 | 18.0 | 18.0 | 18.0 | 18.0 | 18.0 | 18.0 | 18.0 | 18.0 | 18.0 | 18.0 |
| Water | 16.67 | 16.67 | 16.67 | 16.67 | 16.67 | 16.67 | 16.67 | 16.67 | 16.67 | 16.67 | 16.67 | 16.67 |
| Glycerine | 10.0 | 10.0 | 10.0 | 10.0 | 10.0 | 10.0 | 10.0 | 10.0 | 10.0 | 10.0 | 10.0 | 10.0 |
| Sodium Carboxy Methyl Cellulose | 1.0 | 1.0 | 1.0 | 1.0 | 1.0 | 1.0 | 1.0 | 1.0 | 1.0 | 1.0 | 1.0 | 1.0 |
| Flavor | 1.0 | 1.0 | 1.0 | 1.0 | 1.0 | 1.0 | 1.0 | 1.0 | 1.0 | 1.0 | 1.0 | 1.0 |
| Sodium Lauryl Sulfate | 0.8 | 0.8 | 0.8 | 0.8 | 0.8 | 0.8 | 0.8 | 0.8 | 0.8 | 0.8 | 0.8 | 0.8 |
| Titanium Dioxide | 0.5 | 0.5 | 0.5 | 0.5 | 0.5 | 0.5 | 0.5 | 0.5 | 0.5 | 0.5 | 0.5 | 0.5 |
| Sodium | 0.76 | 0.76 | 0.76 | 0.76 | 0.76 | 0.76 | 0.76 | 0.76 | 0.76 | 0.76 | 0.76 | 0.76 |
| Mono Fluoro Phosphate | 0.76 | 0.76 | 0.76 | 0.76 | 0.76 | 0.76 | 0.76 | 0.76 | 0.76 | 0.76 | 0.76 | 0.76 |
| Sodium Saccharin | 0.27 | 0.27 | 0.27 | 0.27 | 0.27 | 0.27 | 0.27 | 0.27 | 0.27 | 0.27 | 0.27 | 0.27 |
| ULTRAMULSION ™ (See Table I) | | | | | | | | | | | | |
| Example 1 | 2.0 | — | — | — | — | — | — | — | — | — | — | — |
| Example 3 | — | 2.0 | — | — | — | — | — | — | — | — | — | — |
| Example 6 | — | — | 2.0 | — | — | — | — | — | — | — | — | — |
| Example 4 | — | — | — | 2.0 | — | — | — | — | — | — | — | — |
| Example 7 | — | — | — | — | 2.0 | — | — | — | — | — | — | — |

TABLE III-continued

TOOTHPASTE COMPOSITIONS
% W/W

| Component | Example # | | | | | | | | | | | |
|---|---|---|---|---|---|---|---|---|---|---|---|---|
| | 22 | 23 | 24 | 25 | 26 | 27 | 28 | 29 | 30 | 31 | 32 | 33 |
| ULTRAMULSION ™ (See Table II) | | | | | | | | | | | | |
| Example 12 | — | — | — | — | — | 2.0 | — | — | — | — | — | — |
| Example 14 | — | — | — | — | — | — | 2.0 | — | — | — | — | — |
| Example 15 | — | — | — | — | — | — | — | 2.0 | — | — | — | — |
| Example 18 | — | — | — | — | — | — | — | — | 2.0 | — | — | — |
| Example 21 | — | — | — | — | — | — | — | — | — | 2.0 | — | — |

TABLE IV

DENTAL FLOSS COMPOSITION
% W/W

| Component | EXAMPLE # | | | | | | |
|---|---|---|---|---|---|---|---|
| | 34 | 35 | 36 | 37 | 38 | 39 | 40 |
| Dicalcium Phosphate Dihydrate | 14.0 | 14.0 | 14.0 | 14.0 | 14.0 | 14.0 | 14.0 |
| Carrageenan | 14.0 | 14.0 | 14.0 | 14.0 | 14.0 | 14.0 | 14.0 |
| Insoluble Saccharin | 2.2 | 2.2 | 2.2 | 2.2 | 2.2 | 2.2 | 2.2 |
| Flavor | 8.9 | 8.9 | 8.9 | 8.9 | 8.9 | 8.9 | 8.9 |
| EDTA | 0.2 | 0.2 | 0.2 | 0.2 | 0.2 | 0.2 | 0.2 |
| Propyl Gallate | 0.1 | 0.1 | 0.1 | 0.1 | 0.1 | 0.1 | 0.1 |
| ULTRAMULSION ™ (See Table I) | | | | | | | |
| Example 4 | 60.6 | — | — | — | — | — | — |
| Example 5 | — | 60.6 | — | — | — | — | — |
| Example 6 | — | — | 60.6 | — | — | — | — |
| ULTRAMULSION ™ (See Table II) | | | | | | | |
| Example 2 | — | — | — | 60.6 | — | — | — |
| Example 3 | — | — | — | — | 60.6 | — | — |
| Example 1 | — | — | — | — | — | 60.0 | — |
| Example 10 | — | — | — | — | — | — | 60.6 |

Each composition was loaded on to 800 denier Nylon Dental floss at between 40–60 mg./yard.

TABLE V

BREATH SPRAY COMPOSITIONS
% W/W

| Component | Example # | | | |
|---|---|---|---|---|
| | 41 | 42 | 43 | 44 |
| Water | 82.75 | 82.75 | 82.75 | 82.75 |
| Sorbitol - 70% Aq. | 8.5 | 8.5 | 8.5 | 8.5 |
| Glycerin | 3.0 | 3.0 | 3.0 | 3.0 |
| Xanthan Gum | 0.4 | 0.4 | 0.4 | 0.4 |
| Sodium Saccharin | 0.4 | 0.4 | 0.4 | 0.4 |
| Sodium Benzoate | 0.3 | 0.3 | 0.3 | 0.3 |
| EDTA | 0.05 | 0.05 | 0.05 | 0.05 |
| Flavor | 0.60 | 0.6 | 0.6 | 0.6 |
| ULTRAMULSION ™ (See Table I) | | | | |
| Example 3 | 4.0 | — | — | — |
| Example 4 | — | 4.0 | — | — |
| Example 5 | — | — | 4.0 | — |
| Example 9 | — | — | — | 4.0 |

Additional specific examples of the oral care products are described in Tables VI and VII.

TABLE VI

DRY MOUTH SPRAY COMPOSITION
Pump Spray
% W/W

| Component | Example # | | |
|---|---|---|---|
| | 45 | 46 | 47 |
| Water | 93.86 | 93.86 | 93.86 |
| Xanthan Gum | 0.7 | 0.7 | 0.7 |
| Sorbitol - 70% Aq. | 3.5 | 3.5 | 3.5 |
| Potassium Chloride | 0.1 | 0.1 | 0.1 |
| Sodium Chloride | 0.06 | 0.06 | 0.06 |
| Calcium Chloride | 0.02 | 0.02 | 0.02 |
| Potassium Phosphate Dihydrate | 0.04 | 0.04 | 0.04 |
| Flavor | 0.06 | 0.06 | 0.06 |
| Propyl Gallate | 0.1 | 0.1 | 0.1 |
| ULTRAMULSION ™ (See Table I) | | | |
| Example 2 | 1.5 | — | — |
| Example 4 | — | 1.5 | — |
| Example 6 | — | — | 1.5 |

TABLE VII

TEETHING GEL
% W/W

| Component | Example # | |
|---|---|---|
| | 48 | 49 |
| Water | 45.7 | 45.7 |
| Sorbitol - 70% Aq. | 34.3 | 34.3 |
| Glycerine | 5.0 | 5.0 |
| Potassium Sorbate | 0.151 | 0.151 |
| Sodium Saccharin | 0.075 | 0.075 |
| Citric Acid | 0.1 | 0.1 |
| Methyl Paraben | 0.15 | 0.15 |
| Propylene Glycol | 10.0 | 10.0 |
| Sodium Carboxy Methyl Cellulose | 2.52 | 2.52 |
| ULTRAMULSION ™ (See Table I) Example 4 | 2.0 | — |
| ULTRAMULSION ™ (See Table II) Example 6 | — | 2.0 |

In addition to the foregoing, other oral care products are included in the present invention, such as chewing gums, prophylactic pastes and denture wearer products to treat stomatitis. While also in the latter the ULTRAMULSION™ dispersion provides the base functioning as a carrier for specific active ingredients such as Candida yeast sp. antifungal agents such as stannous fluoride.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. An oral care composition selected from the group consisting of rinses, sprays, gels, creams, toothpastes, tooth powders, dental floss, interproximal simulators, mints and chewing gum, wherein said composition contains an aqueous-free high shear or ULTRAMULSION™ dispersion, formed by heating a mixture of surfactant and silicone, followed by high shear mixing wherein:

a. the silicone is insoluble in said surfactant, has a viscosity greater than about 100,000 cs, and a particle size up to about 10 microns;

b. the surfactant to silicone ratio in the ULTRAMULSION dispersion is from between about 400:1 and about 1:1; and the surfactant has an orienting effect on the silicone, c. the ULTRAMULSION dispersion forms stable dispersions in aqueous containing oral care compositions, and d. said oral care composition exhibits enhanced substantivity to surfaces in the oral cavity while the dispersed silicone phase of said ULTRAMULSION dispersion functions as a reservoir for one or more lipid soluble and lipid dispersible oral care active ingredients.

2. An oral care composition according to claim 1, wherein said ULTRAMULSION dispersion comprises a nonionic poloxamer surfactant and polydimethylsiloxane wherein:

a. said polydimethylsiloxane has the chemical composition $(CH_3)_3SiO[SiO(CH_3)_2]_nSi(CH_3)_3$, wherein n is a whole number;

b. said surfactant has the chemical composition wherein x, y, and x' are whole numbers;

c. the viscosity of the polydimethylsiloxane ranges from between about 2.5 million and about 50 million cs;

d. the particle size of most of the polydimethylsiloxane in the ULTRAMULSION dispersion is from between about 0.1 and about 10 microns;

e. from between about 80% and 95% of said polydimethylsiloxane particles in the ULTRAMULSION dispersion are from between about 1 and about 10 microns;

f. the nonionic surfactant is a polyoxyethylene-polyoxypropylene block copolymer having a molecular weight from between about 1,100 and about 150,000;

g. the ratio of surfactant to polydimethylsiloxane is from between about 400:1 and about 1:2; and h. the ULTRAMULSION dispersion dispersed in water based oral care composition is stable.

3. A method of manufacturing ULTRAMULSION™ dispersions suitable for oral care compositions said method comprising, heating said surfactant and silicone mixture in a heated, stirred vessel substantially free from water, followed by subjecting said mixture to high shear dispersion; wherein:

a. the silicone is insoluble in said surfactant, has a viscosity ranging from about 100,000 cs up to about 50 million cs, and a particle size up to about 10 microns, b. the surfactant to silicone ratio in the high shear dispersion is from between about 400:1 and about 1:1; and the surfactant has an orienting effect on the silicone, c. the silicone is oriented, exhibits enhanced substantivity to surfaces in the oral cavity and functions as a reservoir for one or more lipid soluble and lipid dispersible hair care active ingredients.

4. A method according to claim 3, wherein the heated vessel is provided with an inert head of gas.

5. A method according to claim 3, wherein said high shear dispersing means is fitted with a small orifice.

6. A method according to claim 3 wherein said high shear dispersing means is an ultrasonication means.

7. A stable aqueous based oral care composition containing a dispersed therein an ULTRAMULSION dispersion comprising a nonionic poloxamer surfactant and a polydimethylsiloxane insoluble in said surfactant wherein:

a. said polydimethylsiloxane has the chemical composition $(CH_3)_3SiO[SiO(CH_3)_2]_nSi(CH_3)_3$, wherein n is a whole number;

b. said surfactant has the chemical composition wherein x, y, and x' are whole numbers;

c. the viscosity of the polydimethylsiloxane ranges from between about 2.5 million and about 50 million cs;

d. the particle size of most of the polydimethylsiloxane in the ULTRAMULSION dispersion is from between about 0.1 and about 10 microns;

e. from between about 80% and 95% of said polydimethylsiloxane particles in the ULTRAMULSION dispersions are from between about 1 and about 10 microns;

f. the nonionic surfactant is a polyoxyethylene-polyoxypropylene block copolymer having a molecular weight from between about 1,100 and about 150,000;

g. the ratio of surfactant to polydimethylsiloxane is from between about 400:1 and about 1:2; and h. the ULTRAMULSION dispersion dispersed in water is stable.

8. An oral care composition according to claim 7, wherein the ratio of said surfactant to said silicone is 9:1 and 90% of the silicone particles are from between about 1 and 3 microns.

9. An oral care composition according to claim 7, wherein the ratio of said surfactant to said silicone is 2:1 and 100% of the silicone dispersion is less than 10 microns.

10. An oral care composition according to claim 7, wherein the ratio of said surfactant to said silicone is 1:1 and the silicone particles in said ULTRAMULSION dispersion are less than 10 microns.

11. An aqueous based rinse composition containing an ULTRAMULSION dispersion comprising a nonionic poloxamer surfactant and polydimethylsiloxane insoluble in said surfactant wherein:

a. said polydimethylsiloxane has the chemical composition $(CH_3)_3SiO[SiO(CH_3)_2]_nSi(CH_3)_3$, wherein n is a whole number;

b. said surfactant has the chemical composition wherein x, y, and x' are whole numbers;
c. the viscosity of the polydimethylsiloxane ranges from between about 100,000 and about 4 million cs;
d. the particle size of most of the polydimethylsiloxane in the ULTRAMULSION dispersion is from between about 0.1 and about 10 microns;
e. from between about 80% and 95% of said polydimethylsiloxane particles in the ULTRAMULSION dispersion are from between about 1 and about 10 microns;
f. the nonionic surfactant is a polyoxyethylene-polyoxypropylene block copolymer having a molecular weight from between about 1,100 and about 150,000;
g. the ratio of surfactant to polydimethylsiloxane is from between about 400:1 and about 1:2;
h. the ULTRAMULSION dispersion dispersed in water based rinse is stable, and
i. the polydimethylsiloxane contains one or more essential oil active ingredients.

12. An oral care composition according to claim 7, wherein the silicone is a polydimethylsiloxane uncoiled and oriented wherein the oxygen moieties are generally oriented in a plane distinct from that of the methyl/moieties.

13. An oral care composition according to claim 1, wherein the surfactant is selected from the group consisting of, flowable liquids of varying viscosities, pastes, prills and cast solids.

14. A method according to claim 3, wherein the high shear dispersion is achieved with high shear dispersing means selected from the group consisting of superfine dispersion means and ultrasonic dispersion means.

15. An oral care composition according to claim 7, wherein the ratio of surfactant to polydimethylsiloxane is 1:1 and at least 80% of the polydimethylsiloxane dispersed particles are between 1 and 9 microns.

16. An oral care composition according to claim 1, wherein the ratio or surfactant to polydimethylsiloxane is 9:1 and about 90% of the polydimethylsiloxane dispersed particles are between 1 and 3 microns.

17. An oral care composition according to claim 1, wherein the ratio or surfactant to polydimethylsiloxane is 2:1 and about 90% of the polydimethylsiloxane dispersed particles are between 1 and 3 microns.

18. An oral care composition according to claim 7, wherein the ratio of surfactant to polydimethylsiloxane is 4:1 and about 90% of the polydimethylsiloxane dispersed particles are between 1 and 9 microns.

19. An oral care composition according to claim 7, wherein the ratio of surfactant to polydimethylsiloxane is 9.5:0.5 and about 100% of the polydimethylsiloxane dispersed particles are between 1 and 9 microns.

20. An oral care composition according to claim 7, wherein the polydimethylsiloxane has a viscosity of 2.5 million cs and the surfactant is a solid at room temperature.

21. An oral care composition according to claim 1, wherein the silicone contains an active ingredient selected from the group consisting of, anti-plaque, anti-tartar, anti-gingivitis and anti-periodontitis active ingredients.

22. An oral care composition according to claim 21, wherein the silicone contains triclosan.

23. An oral care composition according to claim 21, wherein the silicone contains a mixture of essential oils selected from the group consisting of thymol, eucalyptol, menthol and methyl salicylate.

24. An oral care composition according to claim 21, wherein the silicone contains stannous fluoride.

25. An oral care composition according to claim 21, wherein the silicone contains chlorhexidine.

26. An oral care composition according to claim 21, wherein the silicone contains metronidazole.

27. An oral care composition according to claim 1, wherein the composition is a gel for treating periodontal pockets.

28. An oral care composition according to claim 1, wherein the composition is a toothpaste containing triclosan in said silicone.

29. An oral care composition according to claim 1, wherein the composition is a dental floss where the silicone contains one or more antimicrobials selected from the group consisting of stannous fluoride, triclosan, chlorhexidine and metronidazole.

30. An oral care composition according to claim 1, wherein the composition is a gel and the silicone contains benzocaine.

* * * * *